United States Patent [19]
Jones et al.

[11] Patent Number: 5,935,853
[45] Date of Patent: *Aug. 10, 1999

[54] HUMAN EPITHELIAL CELL MATRIX AND USES THEREFOR

[75] Inventors: Jonathan C. R. Jones; Stephanie Stahl, both of Chicago; Sigmund A. Weitzman, Winnetka, all of Ill.

[73] Assignee: Northwestern University, Evanston, Ill.

[*] Notice: This patent is subject to a terminal disclaimer.

[21] Appl. No.: 09/078,438

[22] Filed: May 13, 1998

Related U.S. Application Data

[63] Continuation of application No. 08/626,168, Mar. 29, 1996, Pat. No. 5,770,448.

[51] Int. Cl.⁶ .................................................. C12N 5/00
[52] U.S. Cl. ........................... 435/325; 435/68.1; 623/11; 530/395
[58] Field of Search .................................. 435/325, 68.1; 623/11; 530/395

[56] References Cited

U.S. PATENT DOCUMENTS

| | | |
|---|---|---|
| 5,026,637 | 6/1991 | Soule et al. . |
| 5,206,165 | 4/1993 | Pauley et al. . |
| 5,238,840 | 8/1993 | Pauley et al. . |
| 5,422,264 | 6/1995 | Quaranta et al. . |
| 5,436,152 | 7/1995 | Soule et al. . |
| 5,541,106 | 7/1996 | Jones ....................................... 435/325 |

FOREIGN PATENT DOCUMENTS

| | | |
|---|---|---|
| WO 92/17498 | 10/1992 | WIPO . |
| WO 94/05316 | 3/1994 | WIPO . |
| WO 95/06660 | 3/1995 | WIPO . |

OTHER PUBLICATIONS

Bergstraesser et al., "Expression of Hemidesmosomes and Component Proteins is Lost by Invasive Breast Cancer Cells," *American Journal of Pathology*, vol. 147, No. 6, pp. 1823–1839, (Dec. 1995).

Carter, et al., "Epiligrin, a New Cell Adhesion Ligand for Integrin $\alpha 3\beta 1$ in Epithelial Basement Membranes," *Cell*, vol. 65, pp. 599–610, date (1991).

Chapman, "Abnormal expression of hemidesmosome–like structures by junctional epidermolysis bullosa keratinocytes in vitro," *British Journal Dermatology*, vol. 123, pp. 137–144, (1990).

Giudice, et al., "Cloning and Primary Structural Analysis of the Bullous Pemphigoid Autoantigen BP180," The Society of Investigative Dermatology, Inc., vol. 99, No. 3, pp. 243–250, (Sep. 1992).

Giudice et al., "Identification of Two Collagen Domains within the Bullous Pemphigoid Autoantigen, BP180," *J. Clin. Invest.*, vol. 87, pp. 734–738 (1991).

Hieda, et al., "Identification of a New Hemidesmosomal Protein, HD1: A Major, High Molecular Mass Component of Isolated Hemidesmosomes," *The Journal of Cell Biology*, vol. 116, No. 6, pp. 1497–1506, (Mar. 1992).

Hopkinson et al., "Cytoplasmic Domain of the 180–kD Bullous Pemphigoid Antigen, a Hemidesmosomal Component: Molecular and Cell Biologic Characterization," *J. Invest. Dermatol.*, vol. 99, No. 3, pp. 264–270 (1992).

Hsi, et al., "Monoclonal Antibody $GB_36$ Raised Against Human Trophoblast Recognizes a Novel Epithelial Antigen," *Placenta*, vol. 8, pp. 209–217, (1987).

Jones, et al., "A function for the integrin $\alpha_6\beta_4$ in the hemidesmosome," *Cell Regulation*, vol. 2, pp. 427–438, (Jun. 1991).

Jones, et al., "Hemidesmosomes: Extracellular Matrix/Intermediate Filament Connectors," *Experimental Cell Research*, vol. 213, pp. 1–11 (1994).

Jones et al., "Intermediate filament–plasma membrane interactions," *Current Opinion in Cell Biology*, vol. 3, pp. 127–132, (1991).

Kurpakus, et al., "Surface Relocation of $Alpha_6Beta_4$ Integrins and Assembly of Hemidesmosomes in an In Vitro Model of Wound Healing," *The Journal of Cell Biology*, vol. 115, No. 6, pp. 1737–1750, (Dec. 1991).

Langhofer, et al., "The matrix secreted by 804G cells contains laminin–related components that participate in hemidesmosome assembly in vitro," *Journal of Cell Science*, vol. 105, pp. 753–764, (1993).

Riddelle et al., "Hemidesmosomes in the epithelial cell line 804G: their fate during wound closure, mitosis and drug induces reorganization of the cytoskeleton", *Journal of Cell Science*, vol. 103, pp. 475–490 (1992).

Riddelle, et al., "Formation of Hemidesmosomes In Vitro by a Transformed Rat Bladder Cell Line," *The Journal of Cell Biology*, vol. 112, No. 1, pp. 159–168, (Jan. 1991).

Rouselle, et al., "Kalinin: An Epithelium–Specific Basement Membrane Adhesion Molecule That is a Component of Anchoring Filaments," *The Journal of Cell Biology*, vol. 114, No. 3, pp. 567–576, (Aug. 1991).

Sonnenberg, et al., "Integrin $\alpha 6/\beta 4$ Complex Is Located in Hemidesmosomes, Suggesting a Major Role in Epidermal Cell–Basement Membrane Adhesion," *The Journal of Cell Biology*, vol. 113, No. 4, pp. 907–917, (May 1991).

(List continued on next page.)

*Primary Examiner*—Leon B. Lankford, Jr.
*Attorney, Agent, or Firm*—Sheridan Ross P.C.

[57] ABSTRACT

A method of growing epithelial cells by contacting the cells with the extracellular matrix deposited or secreted by human MCF-10A mammary epithelial cells. The MCF-10A matrix stimulates cell attachment and hemidesmosome formation in epithelial cells contacted therewith. The invention also encompasses the isolated or purified MCF-10A matrix, compositions comprising the matrix, and shaped articles coated with the matrix.

4 Claims, 2 Drawing Sheets

OTHER PUBLICATIONS

Soule, et al., "Isolation and Characterization of a Spontaneously Immortalized Human Breast Epithelial Cell Line, MCF–10¹," *Cancer Research*, vol. 50, pp. 6075–6086, (Sep. 15, 1990).

Staehelin, "Structure and Function of Intracellular Junctions," *International Review of Cytology*, vol. 39, pp. 191–283 (1974).

Stepp, et al., "$\alpha_6\alpha_4$ integrin heterodimer is a component of hemidesmosomes," *Proc. Natl. Acad. Sci. USA*, vol. 87, pp. 8970–8974, (Nov. 1990).

Tait, et al., "Ultrastructural and Immunocytochemical Characterization of an Immortalized Human Breast Epithelial Cell Line, MCF–10¹," *Cancer Research*, vol. 50, pp. 6087–6094, (Sep. 15, 1990).

Verrando, et al., "The new basement membrane antigen recoginzed by the monoclonal antibody GB3 is a large size glycoprotein: modulation of its expression by retinoic acid," *Biochim. Biophys. Acta.*, vol. 942, pp. 45–56, (Apr. 1988).

HUMAN EPITHELIAL CELL MATRIX AND USES THEREFOR

This application is a continuation of application Ser. No. 08/626,168, filed Mar. 29, 1996, now U.S. Pat. No. 5,770,448 the complete disclosure of which is incorporated herein by reference.

This invention was made under a U.S. Army Grant from the Department Of Defense number DAMD 17-94J-4291. The U.S. government may have rights in the invention.

FIELD OF THE INVENTION

The present invention relates to the growth of epithelial cells on an extracellular matrix produced by a human cell line. More specifically, the invention relates to the stimulation of hemidesmosome assembly in epithelial cells by contacting the cells with an extracellular matrix from a human epithelial cell line.

BACKGROUND OF THE INVENTION

When organs of the body are formed, they develop in neatly organized arrays. Often, cell types are separated by connective tissue called basement membranes. In skin, for instance, the superficial layer of epidermal cells adheres to the underlying basement membrane. This skin basement membrane acts as a barrier between the epidermal cells on the outside, and the dermal cells underneath. A similar arrangement of cells occurs in the lining of the gut and in the oral cavity.

Basement membranes have been implicated in the growth, attachment, migration, repair and differentiation of their overlying cell populations. Three layers have been defined in basement membranes: a) the lamina lucida, an electronmicroscopically clear region in close approximation to the overlying cells; b) the lamina densa, an electron dense region of 20–300 nm in width; and c) the sublamina densa which contains anchoring fibrils, microfibrillar bundles and collagen fibers.

Many epithelial cells interact with the underlying extracellular matrix, a network of proteins to which cells attach by a junction called the hemidesmosome (Staehelin, (1974) *Structure and Function of Intercellular Junctions*, Department of Molecular, Cellular and Developmental Biology, University of Colorado, Boulder, Colo., 191–283). The hemidesmosome, with its associated structures, including intermediate filaments and anchoring fibrils, forms an adhesion complex. Disruptions of the epithelial-connective tissue interaction are often accompanied by disruption of the hemidesmosome complex. For example, in certain blistering skin diseases, such as junctional epidermolysis bullosa, where epithelial cell-connective tissue interaction is abnormal, it has been proposed that there is biochemical modification in, or loss of, a basement membrane zone-associated component of the hemidesmosome.

Bullous pemphigoid (BP) is an autoimmune disease which results in a disruption of the interactions between epithelial cells and connective tissue simultaneously with loss of hemidesmosome integrity (Chapman et al., *Br. J. Dermatol.*, 123:137–144, 1990). In particular, it has been determined that BP patients produce auto-antibodies against hemidesmosome components, and two high molecular weight components of the hemidesmosome have been identified and characterized using these BP antibodies (Klatte et al., *J. Cell Biol.*, 109:3377–3390, 1989). One component is a 230 kDa polypeptide (BP230) that may act as an anchor for cytoskeletal elements in the hemidesmosomal plaque (Jones and Green, *Curr. Opin. Cell Biol.*, 3:127–132, 1991). The second component is a 180 kDa type II membrane protein (BP180) which has a collagen-like extracellular domain (Giudice et al., *J. Clin. Invest.*, 87:734–738, 1991); Hopkinson et al., *J. Invest. Dermatol*, 3:264–267, 1992).

In addition, it has been demonstrated that the interaction of the hemidesmosome with the underlying connective tissue involves the $\alpha_6\beta_4$ integrin cell adhesion receptor (Stepp et al., *Proc. Natl. Acad. Sci. USA*, 87:8970–8974, 1990; Jones et al., *Curr. Opin. Cell Biol.*, 3:127–132, 1991; Sonnenberg et al., *J. Cell Biol.*, 113:907–917, 1991; Kurpakus et al., *J. Cell Biol.*, 115:1737–1750, 1991). The $\alpha_6\beta_4$ heterodimer has been localized to hemidesmosomes along the basal surfaces of the 804G rat bladder carcinoma cell line (Jones et al., *Cell Regulation*, 2:427–438, 1991). These results suggest that integrins (e.g., $\alpha_6\beta_4$) may play an important role in the assembly and adhesive functions of hemidesmosomes.

For a recent review describing the molecular structure and assembly of hemidesmosomes, see Jones et al., *Experimental Cell Research*, 213, 1–11 (1994).

It has generally been reported that most epithelial cells do not assemble bona fide hemidesmosomes when cultured in vitro, despite the fact that they appear to express all of the necessary plaque and hemidesmosomal components. Indeed, it is only recently that cell lines, such as the 804G and NBT-II rat bladder carcinoma cell lines, have been found to be capable of assembling hemidesmosomes in vitro under standard culture conditions (Riddelle et al., (1991), *J. Cell Biol.*, 112:159–168; allowed U.S. application Ser. No. 08/152,460, the entire contents of which are hereby incorporated by reference; Jones et al., *Experimental Cell Research*, 213, 1–11 (1994)). Even more recently, Bergstraesser et al. found that primary normal human breast epithelial cells produced hemidesmosomes after prolonged culture in vitro (Bergstraesser et al., *American Journal Of Pathology*, 147, 1823–1839 (December 1995)).

When epithelial cells unable to form hemidesmosomes are plated on the cell matrix deposited by 804G rat bladder carcinoma cells, hemidesmosome formation is induced (Langhofer et al., (1993) *J. Cell Sci.*, 105:753–764; allowed U.S. application Ser. No. 08/324,367, the entire contents of which are hereby incorporated by reference). In addition, U.S. Pat. No. 5,422,264, the entire contents of which are hereby incorporated by reference, discloses that a soluble matrix equivalent produced by 804G cells also induces attachment and hemidesmosome formation in cells contacted with the soluble matrix.

The 804G matrix comprises four glycosylated proteins of approximately 135 kDa, 140 kDa, 150 kDa and 400 kDa and one non-glycosylated protein of about 85 kDa (Langhofer et al., *J. Cell Sci.*, 105, 753–764 (1993); allowed U.S. application Ser. No. 08/324,367). The 140 kDa and 85 kDa proteins are immunologically related to laminin B2t (Langhofer et al., *J. Cell Sci.*, 105, 753–764 (1993)). The 804G matrix and soluble matrix equivalent comprise similar major protein components.

The molecular weights of the 804G matrix elements are similar to those of components of high-molecular-weight complexes of human proteins secreted by keratinocytes. These human complexes are BM600 (described in Verrando et al., *Biochim. Biophys. Acta.*, 942:45–56 (1988) and Hsi et al., *Placenta* 8:209–217 (1987)), kalinin (described in Rouselle et al., *J. Cell Biol.*, 114:567–576 (1991) and Burgeson et al., PCT WO 92/17498 and PCT WO 94/05316), and epiligrin (described in Carter et al., *Cell*, 65:599–610 (1991) and Carter et al., PCT WO 95/06660). In addition, kalinin has been shown to be immunologically related to 804G matrix (Jones et al., *Experimental Cell Research,* 213, 1–11 (1994)). However, kalinin, BM600 and epiligrin, unlike 804G matrix, do not induce hemidesmosome formation.

Because the organization of cells growing on the hemidesmosome-inducing 804G matrix is significantly more advanced and more tissue-like than cells grown without the matrix, it would be desirable to grow epithelial cells for various applications on such a matrix. However, 804G matrix is derived from a rat cell line. For uses related to humans, it would be preferable to use a human matrix. Specifically it would be particularly desirable to use a human cell-derived hemidesmosome-inducing cell matrix for the growth of epithelial cells thereon. The present invention provides such a matrix.

SUMMARY OF THE INVENTION

The present invention includes a method of stimulating hemidesmosome formation in epithelial cells. This method comprises contacting epithelial cells other than MCF-10A with the hemidesmosome-formation-facilitating matrix protein obtainable from MCF-10A cells, whereby the epithelial cells are stimulated to attach to a substrate and produce hemidesmosomes. As used herein "stimulating hemidesmosome formation" includes: (1) inducing epithelial cells which do not normally produce hemidesmosomes to produce them; and (2) accelerating the formation of hemidesmosomes in cells that can produce hemidesmosomes. The epithelial cells may be vertebrate cells, preferably mammalian cells, most preferably human cells. In a preferred embodiment, the substrate is a shaped article, and the shaped article is coated with the matrix protein prior to the contacting step. The contacting step can be performed ex vivo or in vivo.

The invention also includes a method of facilitating the growth of epithelial cells. The method comprises contacting epithelial cells other than MCF-10A cells with the matrix protein obtainable from MCF-10A cells and growing the epithelial cells in contact with the matrix. Preferably, the epithelial cells are mammalian, and more preferably they are human cells. Human skin cells are one example. In one embodiment, the method includes the step of applying the matrix to a shaped article prior to the contacting step. The shaped article may, for example, be adapted for in vivo use. In a preferred embodiment, the shaped article is an implantable prosthesis, such as a transepithelial appliance or a dental prosthesis. Alternatively, the shaped article may be in the form of a sheet or fabric. The growing step can be performed ex vivo, and the method further comprises the step of introducing the epithelial cells in vivo. Alternatively, the growing step can be performed in vivo.

The invention also includes the extracellular matrix protein obtainable from MCF-10A epithelial cells, in isolated or purified form. "Isolated" or "purified" form means separated from MCF-10A cells. "Isolated form" further means separated from other like proteins sufficiently that the hemidesmosome stimulating properties are readily observed. "Purified form" further means at least the degree of purity obtained through electrophoresis, or alternatively means that the protein comprises at least about 20% of the protein in the composition, preferably at least about 40%, most preferably at least about 90% of the protein in the composition.

The invention also includes a shaped article coated with the matrix protein obtainable from MCF-10A cells. The article can comprise any useful shaped article, such as a fabric, a sheet, a prosthesis, an implant, a transepithelial appliance, a dental implant, or a tooth.

Finally, the invention provides a composition for use in growing epithelial cells other than MCF-10A cells. This composition comprises the matrix protein obtainable from MCF-10A cells, in isolated or purified form, and a pharmaceutically-acceptable carrier.

DETAILED DESCRIPTION OF THE PRESENTLY PREFERRED EMBODIMENTS

Figure 1:
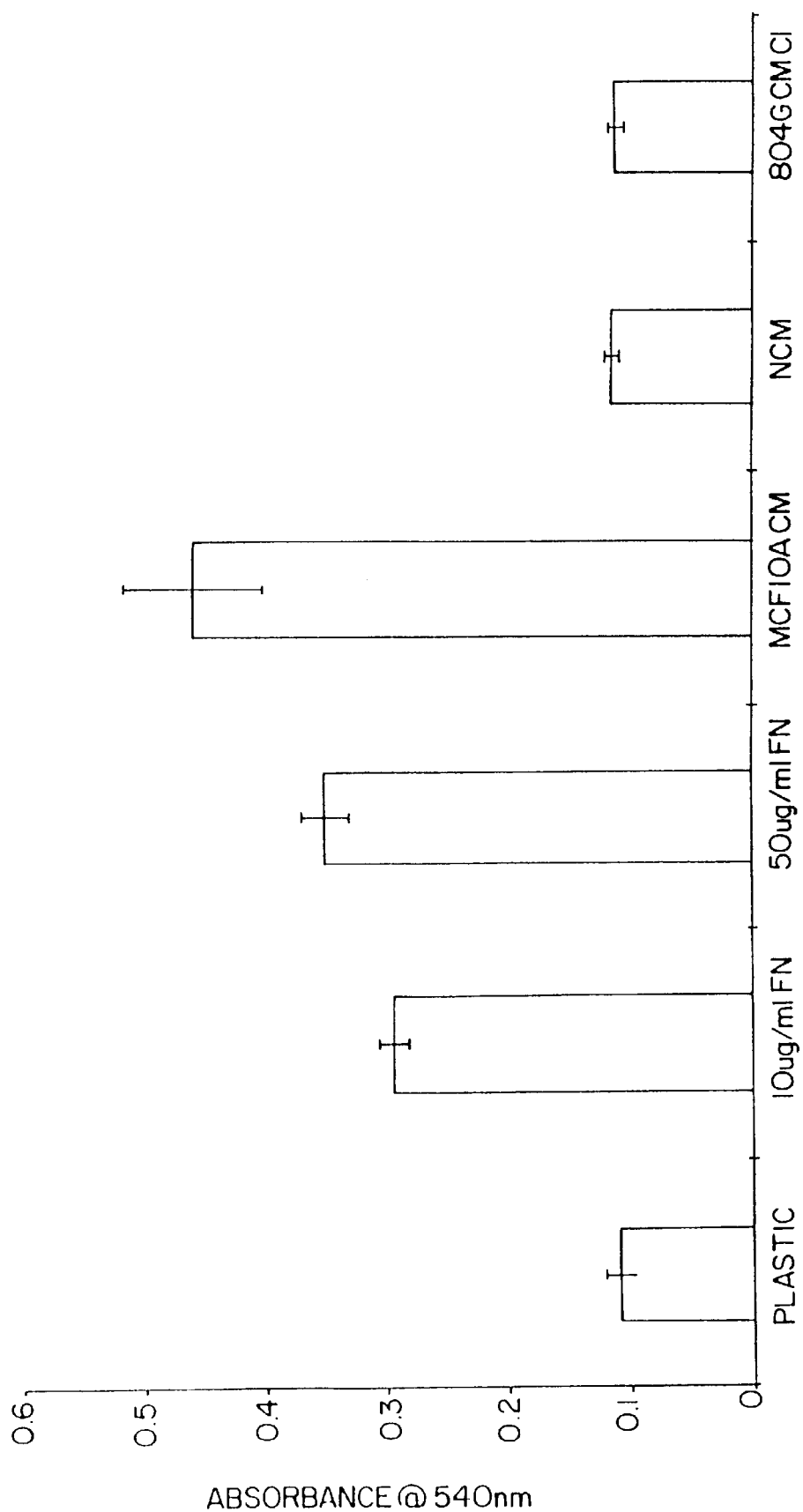
FIG. 1 shows a graph of optical density (indicative of the number of adherent epithelial cells) obtained under various culture conditions.

The present invention includes the discovery that the MCF-10A cell line, an immortalized human mammary epithelial cell line, produces an extracellular matrix which is capable of stimulating hemidesmosome formation in unrelated epithelial cells contacted with the matrix. The MCF-10A cell line produces both a deposited (insoluble) and a secreted (soluble) matrix. The insoluble matrix and the soluble matrix comprise similar major components.

As described in Example 1, MCF-10A cells have been found to be capable of assembling hemidesmosomes when cultured in vitro. This was a surprising finding since it had been reported in the literature that MCF-10A cells did not form hemidesmosomes. Tait et al., *Cancer Research,* 50, 6087–6094 (1990). It was even more surprising, therefore, that MCF-10A cells could produce a matrix which would stimulate hemidesmosome formation in unrelated epithelial cells contacted therewith.

The MCF-10A cell line is available from the American Type Culture Collection, Rockville, Md. (accession number ATCC CRL 10317). The development and properties of the MCF-10A cell line are described in Tait et al., *Cancer Research* 50, 6087–6094 (1990), Soule et al., *Cancer Research,* 50, 6075–6086 (1990), and U.S. Pat. Nos. 5,026, 637 and 5,436,152, the entire contents of which are incorporated by reference. Culture conditions for the MCF-10A cell line are described in these references and Example 1.

Analysis of the MCF-10A matrix indicates that it comprises four major polypeptides having approximate molecular weights of about 450, 150, 135 and 100 kDa as measured by SDS-PAGE. The 450 kDa polypeptide is a heterotrimeric human protein which separates under reducing conditions into the other three polypeptides of 150, 135, and 100 kDa found in the MCF-10A matrix.

The molecular weights of the major components of the MCF-10A matrix are similar to the molecular weights of the major polypeptides that comprise the 804G matrix. Further, polyclonal antiserum generated against the 804G matrix recognizes the 135 and 100 kDa proteins of the MCF-10A matrix.

J21, a polyclonal antiserum generated against the MCF-10A matrix, recognizes proteins of 150, 135 and 100 kDa. Immunoprecipitation of MCF-10A conditioned medium with a monoclonal antibody to laminin 5 reveals bands similar to those recognized by J21.

As noted above, the MCF-10A matrix stimulates hemidesmosome assembly in epithelial cells contacted therewith. For instance, primary human breast epithelial cells normally take 7–14 days to assemble hemidesmosomes in vitro but, in the presence of MCF-10A matrix, they assemble hemidesmosomes in 24 hours (see Example 3). Also, the MCF-10A matrix will induce hemidesmosome assembly in cells which do not normally produce mature hemidesmosomes (see Example 4). The MCF-10A matrix has further been found to induce rapid adhesion of epithelial cells to substrates coated with it (see Examples 6 and 7).

Accordingly, one major use contemplated for the matrix of the present invention is in cell growth and attachment. A substrate upon which cells are to be grown may be coated with the matrix, or with purified hemidesmosome-promoting components thereof. The epithelial cells to be grown are then applied to the substrate, and grown on the matrix. Such cells, including human cells in vitro and in vivo, will grow in an organized fashion on the substrate and will form hemidesmosomes. Hemidesmosome formation is a major advantage because it greatly enhances the attachment of the cells to the substrate.

The substrates useful in the invention may be any desired substrate. For laboratory use, the substrate may be as simple as glass or plastic. For use in vivo, the substrate may be any biologically compatible material on which cells can grow. Suitable substrate materials include shaped articles made of, or coated with, materials such as collagen, polylactic acid, polyglycolic acid, other bioerodible materials, biocompatible metals (such as stainless steel and titanium), ceramic materials (including prosthetic materials such as hydroxylapatite), synthetic polymers (including polyesters and nylons), and virtually any other material to which biological molecules can readily adhere.

A specific use of the present invention is for generating skin for allograft use. Epidermal cells, for example, are seeded onto a substrate of the present invention. These cells are grown on the substrate using conventional skin growth conditions, including nutrients and growth factors. The improvement of the present invention, the use of the MCF-10A hemidesmosome-inducing matrix on the substrate, improves such ex vivo growth of skin over previously described techniques that do not use this matrix.

One particular use of the present invention is the augmentation of epidermal cell adhesion to target surfaces. For example, dental implants may be coated with the MCF-10A matrix to stimulate periodontal cell attachment. Existing teeth may also be coated with the matrix as a treatment for gum (junctional epithelium) disease, such as gingivitis. Where a substrate is made of a natural or synthetic bioerodible material in the form of a sheet or fabric, such as woven or bonded collagen or polylactic acid, the matrix may be applied to the surface thereof or admixed with the composition. Cells may then be grown on the matrix ex vivo to form transplantable or implantable materials; alternatively, the materials may be implanted and cells may be permitted to attach in vivo.

The present invention provides both soluble and insoluble MCF-10A extracellular matrix protein that can promote cell attachment and hemidesmosome assembly in unrelated epithelial cells plated on matrix-coated substrates. Epithelial cells may be directly cultured on the matrix deposited by the MCF-10A cells after removal of the cells. Alternatively, the deposited matrix may be solubilized and isolated and used to coat a substrate. The individual protein components of the MCF-10A extracellular matrix may also be isolated or recombinantly produced and used to coat a substrate, either individually or in combination. Alternatively, the conditioned medium, or matrix or matrix components purified from the conditioned medium, may be used by applying them to a substrate. The coating of any desired surface capable of supporting cell adhesion with MCF-10A matrix is within the scope of the present invention.

In addition to the MCF-10A matrix and the active components thereof, the present invention also includes shaped articles coated with those materials. Preferably, the shaped articles are formed of materials other than glass, and include such forms as sheets, fabrics, prostheses, metal articles, bioerodible articles, and implantable articles.

Furthermore, pharmaceutical preparations of the matrix are contemplated. These preparations can be in any suitable form, and comprise the matrix or active component thereof in combination with any of the well known pharmaceutically-acceptable carriers. The matrix may be harvested by scraping, abrading or treatment with low concentrations of sodium dodecyl sulfate (SDS) from surfaces on which the MCF-10A cells have been grown. Alternatively, the matrix may be prepared synthetically through recombinant DNA techniques, or by purification of deposited matrix material. Medium conditioned by MCF-10A cells or matrix or matrix components purified from the conditioned medium can also be used. Carriers include injectable carriers, topical carriers, transdermal carriers and the like. The preparation may advantageously be in a form for topical administration, such as an ointment, gel, cream, spray, dispersion, suspension or paste. The preparations may further include preservatives, antibacterials, antifungals, antioxidants, osmotic agents, and similar materials in composition and quantity as is conventional. For assistance in formulating the compositions of the present invention, one may refer to Remington's Pharmaceutical Sciences, 15th Ed., Mack Publishing Co., Easton, Pa. (1975).

EXAMPLES

Example 1

Hemidesmosome Formation by MCF-10A Cells

This example describes the formation of hemidesmosomes by MCF-10A cells.

MCF-10A Cells: MCF-10A cells were obtained from ATCC, Rockville, Md., accession number CRL 10317. The development and properties of the MCF-10A cell line are described in Tait et al., *Cancer Research*, 50, 6087–6094 (1990), Soule et al., *Cancer Research*, 50, 6075–6086 (1990), and U.S. Pat. Nos. 5,026,637 and 5,436,152.

Culture Medium For MCF-10A Cells: Culture medium containing 1.05 mM $Ca^{+2}$ was prepared by mixing equal amounts of Dulbecco's modified Eagle's medium and Ham's nutrient mixture F-12 containing L-glutamine and 4.5 g/L glucose (GIBCO, Grand Island, N.Y.). Sterilization of this medium (designated DMEM-H) by filtration through 0.22 $\mu$M Millipore filters was followed by the addition of 5% equine serum (GIBCO). The medium was further supplemented with 10 $\mu$g/ml insulin, $1.4 \times 10^{-6}$ M cortisol (Sigma Chemical Co., St. Louis, Mo.), 100 ng/ml cholera enterotoxin (ICN Biomedicals, Cleveland, Ohio), and 20 ng/ml epidermal growth factor (Collaborative Research, Bedford, Mass.). This culture medium was used for all cultures of MCF-10A cells.

Electron Microscopy: MCF-10A cells were cultured for 1, 2 and 7 days at 37° C. on untreated glass coverslips or tissue culture plastic and analyzed by electron microscopy (EM). EM was performed using standard methodology. See, Hyat,

*Basic Techniques For Transmission Electron Microscopy* (Hyat, ed. Academic Press 1986); Riddelle et al., *J. Cell. Biol.*, 112, 159–168 (1991). Briefly, the cultured cells were fixed in 1.0% glutaraldehyde in sodium cacodylate buffer, pH 7.4, for one hour at room temperature, postfixed in 1% $OsO_4$ (Electron Microscopy Sciences (EMS), Fort Washington, Pa.), dehydrated and infiltrated with propylene oxide (EMS) and embedded in Epon-Araldite resin 812 (Tousimis, Rockville, Md.). Thin sections were cut perpendicular to the growth substrate on a Reichert Ultracut E microtome (Reichert Instruments, Buffalo, N.Y.), mounted on 300 mesh copper grids, stained with uranyl acetate and lead citrate (EMS) and viewed at 80 kV in a JEOL 100CX electron microscope (JEOL USA, Peabody, Mass.).

On average, one or more hemidesmosomes could be observed by EM in each MCF-10A cell cross-sectional profile one day after plating. At seven days after plating, at least four hemidesmosomes were observed in each cell. These hemidesmosomes all had a tripartite cytoplasmic plaque to which keratin intermediate filaments attached. Underlying each hemidesmosome was a sub-basal dense plate cross section.

Immunofluorescence: MCF-10A cells were grown on glass coverslips, washed three times in phosphate-buffered saline, pH 7.4, containing 0.2 g/L KCl, 0.2 g/L $KH_2PO_4$, 8.0 g/L NaCl, 1.15 g/L $Na_2HPO_4$ (PBS), fixed for 2–3 minutes in $-20°$ C. acetone, and air dried.

The fixed cells were first incubated in a mixture of primary antibodies for 1 hr at 37° C. The coverslips were extensively washed in PBS and then overlaid with appropriate rhodamine and fluorescein conjugated secondary antibodies by well known methods. The cells were viewed on a Zeiss laser scan microscope (LSM10) equipped with Argon and HeNe lasers for dual fluorescence confocal imaging (Carl Zeiss, Thornwood, N.Y.).

The following primary antibodies were used:

(1) 10C5, an antibody to BP230; preparation described in Hopkinson et al., *Biochem. J.*, 300, 851–857 (1992).

(2) J17, an antibody to BP180; preparation described in Hopkinson et al., *J. Invest. Dermatol.*, 99, 264–270 (1992).

(3) GOH3, an antibody to $\alpha^6$ integrin subunit; purchased from Immunotech, Westbrook, Me.

(4) 3E1, an antibody to $\beta_4$ integrin subunit; purchased from GIBCO, Grand Island, N.Y.

(5) 417D1, an antibody to IFAP 300 (IFAP 300 is an intermediate filament associated protein of about 300 kDa (Jones et al., *Exp. Cell Res.*, 213, 1–11 (1994)); preparation of antibody described in Yang et al.,*J. Cell Biol.*, 10, 620–631 (1985).

As controls for the immunofluorescence analysis, cells were incubated in normal human, mouse or rabbit IgG, as well as secondary antibodies alone, in order to assess staining due to non-specific antibody binding.

As determined by immunofluorescence, the MCF-10A cells expressed all of the major proteins so far identified as hemidesmosomal components ($\alpha_6$, $\beta_4$, BP180, BP230, IFAP 300). These proteins exhibited a polarized basal distribution and were organized into a "cat paw"-like pattern.

Western Blots: The MCF-10A cells were removed from the substrate as described in Example 2, and the material deposited on the substrate by the MCF-10A cells was harvested by scraping. Western blot analysis was performed on the harvested material as described in Example 2, but using the antibodies to $\alpha_6$, $\beta_4$, BP180, BP230 and IFAP 300 identified above. The results of the Western blots also showed that the MCF-10A cells expressed all of the major proteins so far identified as hemidesmosomal components ($\alpha_6$, $\beta_4$, BP180, BP230, IFAP 300).

Example 2

Preparation and Characterization Of MCF-10A Insoluble Matrix

Matrix Preparation: MCF-10A cells were grown for five days on either plastic Petri dishes or glass coverslips. The culture medium was then discarded and the cells washed in sterile PBS. The cells were removed from their matrix by treatment for 5 minutes with sterile 20 mM $NH_4OH$, followed by three rapid washes with sterile distilled water according to the method of Gospodarowicz, in *Methods For Preparation Of Media, Supplements And Substrata*, volume 1, pages 275–293 (Barnes et al. eds. 1984). The matrix was removed from the substrate by solubilization in 8M urea, 1% sodium dodecyl sulfate (SDS) in 10 mM Tris, pH 6.8.

SDS-PAGE: The MCF-10A matrix polypeptide profile was analyzed by SDS polyacrylamide gel electrophoresis (SDS-PAGE) using routine experimental methods known to those with skill in the art. See, e.g., Laemmli, *Nature*, 227, 680–685 (1970). Approximately 20 µg of the solubilized MCF-10A cell matrix was loaded onto an acrylamide gel and electrophoresed. Following gel electrophoresis, the proteins were stained with silver stain.

Under reducing conditions, three major polypeptides were observed. These polypeptides have approximate molecular weights of 150, 135 and 100 kDa. Under non-reducing conditions, a fourth major polypeptide having an approximate molecular weight of 450 kDa was observed.

Western Blots: After SDS-PAGE, the separated polypeptides were transferred to nitrocellulose and probed with the antibodies indicated below by standard well known methods. See, e.g., Towbin et al., *Proc. Natl. Acad. Sci. USA*, 76, 4350–4354 (1979) and Zackroff et al., *J. Cell. Biol.*, 98, 1231–1237 (1984).

(1) GB3 antibody against human laminin 5 γ2 chain (preparation described in Matsui et al., *J. Invest. Dermatol.*, 105, 648 (1995)) recognized the 100 kDa polypeptide, indicating that MCF-10A matrix contains laminin 5-related protein.

(2) J18 antiserum against 804G matrix (prepared as described in Langhofer et al.,*J. Cell Sci.*, 105, 753–764 (1993)) recognizes the 135 and 100 kDa polypeptides. Thus the components of MCF-10A matrix and 804G matrix are immunologically related.

(3) J21 antiserum against the MCF-10A matrix contained antibodies reactive with matrix proteins having approximate molecular weights of 150, 135 and 100 kDa. J21 was prepared in the same manner as J18 using solubilized MCF-10A matrix in place of solubilized 804G matrix (see previous paragraph and Langhofer et al.).

Example 3

Acceleration of Hemidesmosome Formation by MCF-10A Matrix

MCF-10A cells were grown for five days and the cells were removed from their matrix with $NH_4OH$ as described in Example 2. Cell remnants were washed from the substrate with PBS. Primary human epithelial cells derived from reduction mammoplasties (obtained from Northwestern Memorial Hospital, Evanston Hospital, or the Cooperative Human Tissue Network of the National Cancer Institute) were applied to this MCF-10A matrix and cultured for 24 hours as described in Bergstraesser et al., *American Journal Of Pathology*, 147, 1823–1839 (1995). After 24 hours in culture, the primary epithelial cells were processed for EM as described in Example 1. EM showed that the primary epithelial cells assembled hemidesmosomes exhibiting a typical ultrastructure.

In parallel control studies, the primary epithelial cells did not assemble hemidesmosomes when maintained for 24 hours on substrates coated with rat tail collagen. In the control cultures, hemidesmosome formation was first observed after 7 days in culture. See also, Bergstraesser et al., *American Journal Of Pathology*, 147, 1823–1839 (1995). Thus, MCF-10A matrix greatly accelerates the formation of hemidesmosomes in human mammary epithelial cells.

Example 4

Induction of Hemidesmosome Formation by MCF-10A Matrix

Human epidermal carcinoma cells SCC12 do not assemble bona fide hemidesmosomes in vitro. This example examined the effects of MCF-10A matrix on the assembly of hemidesmosomes by SCC12 cells.

MCF-10A matrix was prepared as described in Example 3, and SCC12 cells were cultured on the matrix for 24 hours. SCC12 cells were obtained from Dr. Amy Paller, Childrens' Memorial Hospital, Chicago, Ill. They were cultured in Keratinocyte Growth Medium (Clonetics Corp., San Diego, Calif.) or Minimum Essential Medium (MEM) containing 10% fetal calf serum (GIBCO). As controls, SCC12 cells were plated onto glass. After 24 hours, the cells were analyzed by immunofluorescence as described in Example 1, except that only antibody to the $\alpha_6$ integrin subunits was used.

In SCC12 cells maintained for 24 hrs on glass, the $\alpha_6$ integrin subunits localized to the periphery of the cells. In SCC12 cells maintained on the MCF-10A cell matrix, the $\alpha_6$ integrin subunit showed a dramatically different pattern of distribution. They exhibited "cat paw"-like patterns similar to those seen in MCF-10A cells (see Example 1).

Example 5

Preparation and Characterization of MCF-10A Soluble Matrix

This example describes the preparation of MCF-10A soluble matrix. This soluble matrix was found to contain major components corresponding to those found in insoluble MCF-10A matrix.

Preparation Of CM: MCF-10A cells were grown for six days on either plastic Petri dishes or glass coverslips to form monolayers. Six-day conditioned medium (CM) was collected and frozen.

SDS-PAGE: The polypeptide profile of the MCF-10A CM was analyzed by SDS-PAGE in the same manner as for the insoluble matrix. The CM was found to contain major components corresponding to those found in the MCF-10A insoluble matrix. The major polypeptides in MCF-10A CM had approximate molecular weights of 450, 150, 135 and 100 kDa.

Western Blots: After SDS-PAGE, the separated polypeptides were transferred to nitrocellulose and probed with the antibodies indicated below.

(1) J18 antiserum against 804G matrix was found to recognize polypeptides having approximate molecular weights of 135 and 100 kDa. Thus, the components of the MCF-10A CM and the 804G matrix are immunologically related.

(2) J21 antiserum against the MCF-10A insoluble matrix reacted with proteins in the CM having approximate molecular weights of 150, 135 and 100 kDa. J21 reacted with proteins having the same approximate molecular weights in the insoluble matrix (see Example 2).

Immunoprecipitation: Immunoprecipitation of the MCF-10A CM was performed using conventional methodology. In brief, the CM was clarified by centrifugation and incubated with monoclonal antibody GB3 specific for human laminin 5. The resulting antibody-antigen complexes were immunoprecipitated with *Staphylococcus aureus* Protein A by methods known to those with skill in the art. The immunoprecipitated molecules were separated by SDS-PAGE and transferred to a Western blot as described in Example 2. The gel was immunoblotted with goat anti-mouse antibodies, conjugated to HRP for visualization.

Immunoprecipitation of the MCF-10A CM with GB3 monoclonal antibody specific for human laminin-5 showed a similar ladder of bands as recognized by J21 antiserum to MCF-10A matrix. Again, this suggests that MCF-10A cells are producing laminin 5-related proteins.

Example 6

Induction of Rapid Cell Adhesion by MCF-10A Matrix

The purpose of this experiment was to determine whether or not MCF-10A CM would cause the rapid attachment of FGMet2 human pancreatic carcinoma cells (Kaiui et al., *EMBO J.*, 8, 673–680 (1989)).

Individual wells of a 96 well plate were coated with 100 $\mu$L of MCF-10A CM (prepared as described in Example 5) mixed 1:1 with PBS. Other wells were coated with 804G CM (prepared as described in U.S. Pat. No. 5,422,264). Control wells were coated with either control medium (NCM), 10 $\mu$g/mL fibronectin (FN) in PBS, 50 $\mu$g/mL FN in PBS, or with nothing, and plates were incubated overnight at 4° C. The supernatants were removed, and the wells were washed 3 times with PBS. Then the wells were incubated for 1 hour at 37° C. with PBS plus 1% bovine serum albumin (BSA). FGMet2 cells were then trypsinized (0.02%), washed once in PBS, counted, and resuspended in serum-free medium (DMEM+25 mmol HEPES) at $1.6 \times 10^6$ cells/mL. 50 $\mu$L of this suspension were added to each well, and the plates were incubated at 37° C. for 45 minutes. Non-adherent cells were removed by washing thoroughly with PBS, and adherent cells were fixed with 3.7% formaldehyde in PBS for 15 minutes at room temperature. Formaldehyde was removed and cells were stained with 100 $\mu$L/well 0.5% crystal violet in 20% methanol for 15 minutes at room temperature. The wells were washed abundantly with distilled $H_2O$, dried thoroughly, and the crystal violet was solubilized in 100 $\mu$L 1% SDS in distilled $H_2O$. The plates were read on a plate reader at 540 nm.

As can be observed in FIG. 1, there is a 4.5 fold increase in adhesion of FGMet2 cells when plated on wells pre-coated with MCF-10A CM as compared with uncoated or control medium wells.

Example 7

Induction of Rapid Cell Adhesion by MCF-10A and 804G Soluble Matrices

This example shows the rapid adhesion of FGMet2 pancreatic carcinoma cells to microtiter wells coated with either MCF-10A or 804G CM. 804G CM was prepared as described in U.S. Pat. No. 5,422,264.

Microtiter wells were incubated with 1% BSA in PBS for 1–2 hours at room temperature to block nonspecific protein binding sites. CM (3-fold serial dilutions) was applied to the wells and incubated either at 4° C. overnight or for at least 2 hours at room temperature. The supernatants were removed, and the wells were washed with PBS. FGMet2 cells, 100 μL of 1.6×10$^6$ cells/mL in serum free medium, were added to each well, and the plates were incubated at 37° C. for 30 minutes. Non-adherent cells were removed by washing gently with PBS, and adherent cells were fixed with 100 μl paraformaldehyde solution. After removal of paraformaldehyde, the wells were stained with 100 μl 0.5% crystal violet solution for 15 minutes. After removal of the dye, the wells were washed abundantly with distilled water, followed by solubilization of the dye with 100 μl 1% SDS solution. The absorbance of the wells was measured using a microplate reader at 595 nm, subtracting the absorbance obtained at 405 nm.

Figure 2:
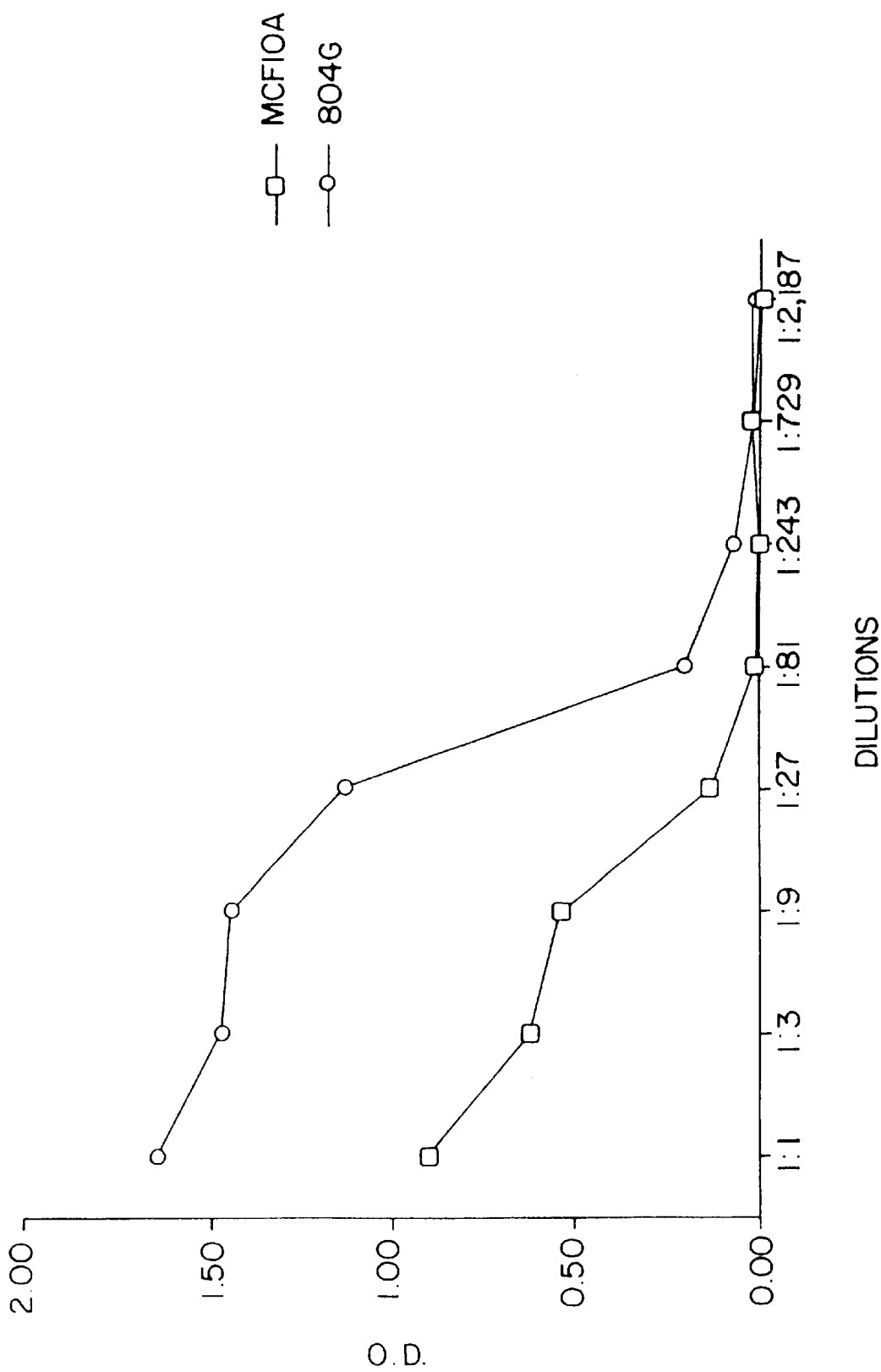
FIG. 2 shows a graph of optical density (indicative of the number of adherent epithelial cells) versus dilution of MCF-10A or 804G conditioned medium.

The graph in FIG. 2 compares the dilution of CM against the relative number of adherent cells. The higher the intensity (O.D. reading), the more cells which adhered to the wells. The difference in rapid adhesion values between 804G and MCF-10A CM may be due to a concentration difference and/or differing culture conditions.

What is claimed is:

1. A transepithelial appliance coated with the matrix protein obtainable from MCF-10A human epithelial cells, the protein having the following characteristics:

it is capable of stimulating hemidesmosome formation; and it comprises polypeptides having molecular weights of about 100 kDa, 135 kDa, and 150 kDa as determined by polyacrylamide gel electrophoresis under reducing conditions.

2. A method for generating skin for allograft use, comprising the steps of:

coating a substrate with the matrix protein obtainable from MCF-10A human epithelial cells, the protein having the following characteristics:

it is capable of stimulating hemidesmosome formation; and it comprises polypeptides having molecular weights of about 100 kDa, 135 kDa, and 150 kDa as determined by polyacrylamide gel electrophoresis under reducing conditions; and contacting said matrix protein-coated substrate with epidermal cells.

3. The method of claim 2 wherein the skin is human skin.

4. A method for stimulating periodontal cell attachment to a tooth or dental implant, comprising the steps of:

coating said tooth or dental implant with the matrix protein obtainable from MCF-10A human epithelial cells, the protein having the following characteristics:

it is capable of stimulating hemidesmosome formation; and it comprises polypeptides having molecular weights of about 100 kDa, 135 kDa, and 150 kDa as determined by polyacrylamide gel electrophoresis under reducing conditions.

* * * * *